United States Patent
Köhler et al.

(10) Patent No.: US 7,440,551 B2
(45) Date of Patent: Oct. 21, 2008

(54) COMPUTER TOMOGRAPH WITH OPTOELECTRONIC DATA TRANSFER

(75) Inventors: Thomas Köhler, Norderstedt (DE); Tim Nielsen, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 148 days.

(21) Appl. No.: 10/576,318

(22) PCT Filed: Oct. 11, 2004

(86) PCT No.: PCT/IB2004/052044

§ 371 (c)(1),
(2), (4) Date: Apr. 18, 2006

(87) PCT Pub. No.: WO2005/040777

PCT Pub. Date: May 6, 2005

(65) Prior Publication Data

US 2007/0080298 A1  Apr. 12, 2007

(30) Foreign Application Priority Data

Oct. 23, 2003  (EP) ............................... 03103928

(51) Int. Cl.
*H05G 1/28* (2006.01)
*H05G 1/60* (2006.01)

(52) U.S. Cl. ........................ 378/166; 378/4; 378/165

(58) Field of Classification Search ................ 378/4, 378/15, 65, 19, 196, 197, 165, 166, 206; 250/551, 217, 208.1

See application file for complete search history.

(56) References Cited

U.S. PATENT DOCUMENTS

| 4,796,183 A | * | 1/1989 | Ermert et al. ................. 378/10 |
| 5,287,117 A | * | 2/1994 | Poslusny .................... 343/763 |
| 5,354,993 A | * | 10/1994 | Kedmi et al. ................ 250/551 |
| 6,718,005 B2 | * | 4/2004 | Hamada et al. .............. 378/15 |

FOREIGN PATENT DOCUMENTS

EP  0 336 167 A2  10/1989

* cited by examiner

*Primary Examiner*—Irakli Kiknadze

(57) ABSTRACT

The invention relates to a computer tomograph, in which data from a rotor, which during operation of the computer tomograph rotates about an axis of rotation, is transferred optoelectronically. For that purpose, on the rotor there is located at least one transmitter, which transmits light towards a receiver mounted on the axis of rotation, the light being modulated with the data to be transferred.

11 Claims, 2 Drawing Sheets

COMPUTER TOMOGRAPH WITH OPTOELECTRONIC DATA TRANSFER

The invention relates to a computer tomograph, in which data is transferred from a rotor optoelectronically.

Known computer tomographs, such as X-ray computer tomographs or SPECT systems (Single Photon Emission Computer Tomography), comprise a sampling unit, the so-called gantry. As a rule, the gantry contains an annular rotor and a stator, in which the rotor is rotatably mounted. The object to be examined or a part thereof is positioned inside the rotor. In a SPECT system, several detectors (for example, gamma cameras) are attached to the rotor. To acquire the image data of the object to be examined the rotor is set rotating and the emission coming from the object to be examined, which emission derives from previously injected radioactive material, is detected. Using known algorithms, the electrical signals supplied by the detector are reconstructed into images.

In the case of an X-ray computer tomograph, at least one X-ray source as well as at last one X-ray image detector are attached to the rotor. To generate sectional images or volume images of the object to be examined, the rotor rotates around the object, during which the X-rays coming from the X-ray source penetrate the object from different angles and are detected by the X-ray image detector. The X-ray image detector converts the X-rays into electrical signals, from which images are reconstructed by a reconstruction unit using known reconstruction algorithms.

Depending on the construction of the computer tomograph, the reconstruction unit is located on the stator, so that the signals generated by the detector have to be transferred as data from the rotor to the stator. Alternatively, computer tomographs are also known in which at least a part of the reconstruction unit is mounted on the rotor, so that already partially processed data or data of entire images are transferred from the rotor for further processing (for example, for visualization). In many systems, in addition to data that contains image information, monitoring or control data of the system is also transferred from the rotor.

The data is transferred from the rotating rotor to the stator, for example, by means of mechanical slip rings. Such mechanical slip rings are often unreliable or susceptible to failure. Alternatively, optical slip rings are used, but they require complicated optics for light deflection. In addition, angle-dependent running lengths or running times of the light in the optical wave guides are problematical here.

With X-ray computer tomographs, a trend towards the use of multi-line detectors is at present being observed, in order for example, to be able to acquire a greater amount of data per revolution of the rotor. This causes an enormous increase in the data to be transmitted per unit of time, however. For that purpose, in the case of previous systems the number of slip rings is increased, which is unsatisfactory from the point of view of economics and further increases susceptibility to failure.

European Patent Application EP0336167 discloses an optoelectronic coupling system for computer tomographs having an optical wave guide. The optical wave guide is of flexible, yet torsionally stable, construction and at its one end is fixedly connected to a light-emitting transmitter. Its other end is fixed in the lateral parts of a rotary bearing, which is rigidly connected eccentrically with a support rotatable about an axis of rotation. The drawback of such a system, however, is that on rotation of the support the optical wave guide rotates whip-like around the object to be examined.

It is an object of the present invention to develop an inexpensive and simple method of transferring data from the rotor of the gantry.

That object is achieved in accordance with claim 1 by a computer tomograph having a gantry, which contains a rotor rotating in the operating state about an axis of rotation, having at least one transmitter attached to the rotor for transmitting data-modulated light in the direction of the axis of rotation and having at least one receiver mounted on the axis of rotation for receiving the data-modulated light transmitted through the free space by the transmitter.

Attached to the rotor is at least one transmitter, which is provided for transmitting light in the direction of the axis of rotation. For data transfer, the light is modulated with the data to be transferred, wherein known means and methods such as amplitude modulation can be used.

The term "light" is to be understood broadly here. For example, light from the visible or invisible spectral region can be used, as well as light having a broad spectrum, monochromatic light or laser light (photons in the same phase). The light can be transmitted by the transmitter as a line-form or conical light beam. In order to influence the transmitter element, the actual light source, contained in the transmitter, the transmitter can comprise additional means (mirrors, lenses, etc.) for influencing the light generated by the transmitter element, in order, for example, to shape the light beam emerging from the transmitter.

A receiver that receives the light transmitted through free space by the transmitter is located on the axis of rotation. The receiver can at the same time be coupled mechanically to the computer tomograph, for example, by a hoop-like holding means. Alternatively, however, it is possible to fix the receiver in the vicinity of the computer tomograph, for example, to a wall. In addition to the actual light-sensitive receiving element, the receiver can also contain means for influencing the transmitted light (mirrors, lenses, etc.).

In the arrangement according to the invention of transmitter and receiver it is ensured that the conditions for the propagation of light, and hence for the transmission of data, are virtually the same for each angle of rotation of the rotor and are hence virtually independent of the angle of rotation of the rotor. For example, the light covers the same path length from transmitter to receiver from each angle of rotation. Problems of running lengths and running times of the light dependent on angle of rotation, such as may occur in the case of optical slip rings, are therefore avoided.

Such an arrangement according to the invention is especially economic compared with known systems since all components can be manufactured at reasonable cost and can be integrated in a structurally simple manner in a computer tomograph. This is further enhanced by the considerable flexibility in the choice of mounting points for the transmitter and the receiver.

With the progress of new technologies for X-ray image detectors, there are occasions when older computer tomographs have to be equipped with a new detector. If this is associated with the transfer of an increased amount of data per unit of time from the rotor, then the existing slip rings are as a rule incapable of such a task. To get round this limitation, it is possible to install further slip rings, but considerable mechanical problems have to be solved here since the computer tomograph is not normally designed to be extended in this way. It has been shown, however, that the construction according to the invention of a computer tomograph can be retrofitted in the case of older apparatuses in an especially easy and inexpensive manner, since the necessary components take up little space and the position of the components can as a rule be defined with such flexibility that an especially simple integration in existing mechanical structures is possible. For example, the mounting position of the transmitter on the rotor and that of the receiver along the axis of rotation can be chosen virtually at will. One must merely ensure that the transmitter transmits the light in the direction of the axis of rotation, the receiver is able to receive the light and under normal use of the computer tomograph the object to be examined does not mask the light.

If the object to be examined is a patient, then in the case of the arrangement disclosed in EP0336167 there is a risk that the patient will be injured or the light guide will be damaged if the patent gets caught in the "flight path" of the light guide. The operating personnel also face the same risk. A similar situation can occur in the case of a computer tomograph for baggage inspection, when, for example, an item of baggage slides unexpectedly off the conveyor belt. In the case of the present invention, however, if a person or an object enters the light path then the transmission of light is merely partially or completely interrupted, whereby the person is not injured (or the item of baggage damaged) nor is the arrangement damaged.

To prevent the transfer of data from being interrupted when the light is covered, in accordance with claim 2, for example two transmitters are attached to the rotor. The light of both transmitters is modulated in the same phase with the same data. If a person in the vicinity of the rotor now holds his hand between rotor and receiver, so that on rotation of the rotor his hand is located at times between one of the transmitters and the receiver and consequently masks the light of this transmitter, then the light of the second transmitter, which is attached to the rotor offset with respect to the first transmitter, reaches the receiver. The receiver is of such sensitive construction that the light intensity of the light from just one transmitter is sufficient for data transfer. Another option for avoiding interruption of the data transfer is a transmitter according to claim 3, especially in combination with claim 10.

In order to be able to use a plurality of channels in parallel for data transfer, the spectrum of the transmitted light is divided in accordance with claim 4 into a plurality of regions. For that purpose, a transmitter for example according to claim 5 can contain a plurality of transmitter elements each having a different spectrum. Such a transmitter element contains, for example, a light source with a narrow spectrum or a light source with a broad spectrum and a filter. The light of the transmitter elements is modulated in each case with different data and transmitted towards a receiver, which can be constructed according to claim 9. Alternatively, the light of the transmitter elements in combination with claim 10 can also be transmitted towards a respective different receiver, each receiver being constructed to receive one of the spectral regions. Receivers according to claim 9 contain, for example, broadband receiving elements with different filters, or several narrow-band receiving elements. An alternative to a construction with a plurality of parallel channels comprises, according to claim 6, mounting a plurality of transmitters on the rotor, each transmitter transmitting light of a respective spectral region. Here too, the receivers can be constructed according to claim 9 and/or 10.

Especially when using transmitters that transmit light in the form of a thin light beam (for example lasers), the light may not strike the receiver exactly or the transmitting direction may run slightly out of alignment during the course of operation. In order to avoid interruption of the data transfer associated therewith, the receiver can be constructed in accordance with claim 7. In front of the actual receiving element for the light there is, for example, a diffusion disk, which enlarges the cross-section of the impinging light beam, or a system of lenses, which deflects the light beam to its focal point, where the receiving element is arranged. Such optical means can also consist of a bundle of light guides, the first ends of which are arranged within a plane on which the light beam impinges and the second end of which terminates in front of the receiving element of the receiver.

If the transmitter is constructed in accordance with claim 8, then the light intensity of the transmitted light at the receiver is especially great and extraneous light from the surroundings also received by the receiver has a less disruptive effect.

In medicine, computer tomographs are frequently constructed with a pivotable gantry, in order to be able to change the plane of image data acquisition. When performing the pivoting movement and in the case of a fixed receiver, the position of the axis of rotation relative to the receiver is changed, so that the light can no longer be received by the receiver. With the construction of the invention according to claim 11 on the other hand, the receiver is caused to track the pivoting movement correspondingly. This is possible, for example, by virtue of a fixed mechanical coupling of the receiver with the gantry. If the receiver is fixed to a wall, then in the case of small pivoting angles it can be moved on the wall corresponding to the pivoting movement, for example, by means of an electronically controlled rail system. Alternatively, it is possible to construct the receiver in accordance with claim 7 and to configure the optical means in such a way that the light is able to reach the receiving element even when the axis of rotation is shifted.

These and other aspects of the invention are apparent from and will be elucidated with reference to the embodiments described hereinafter.

Figure 1:
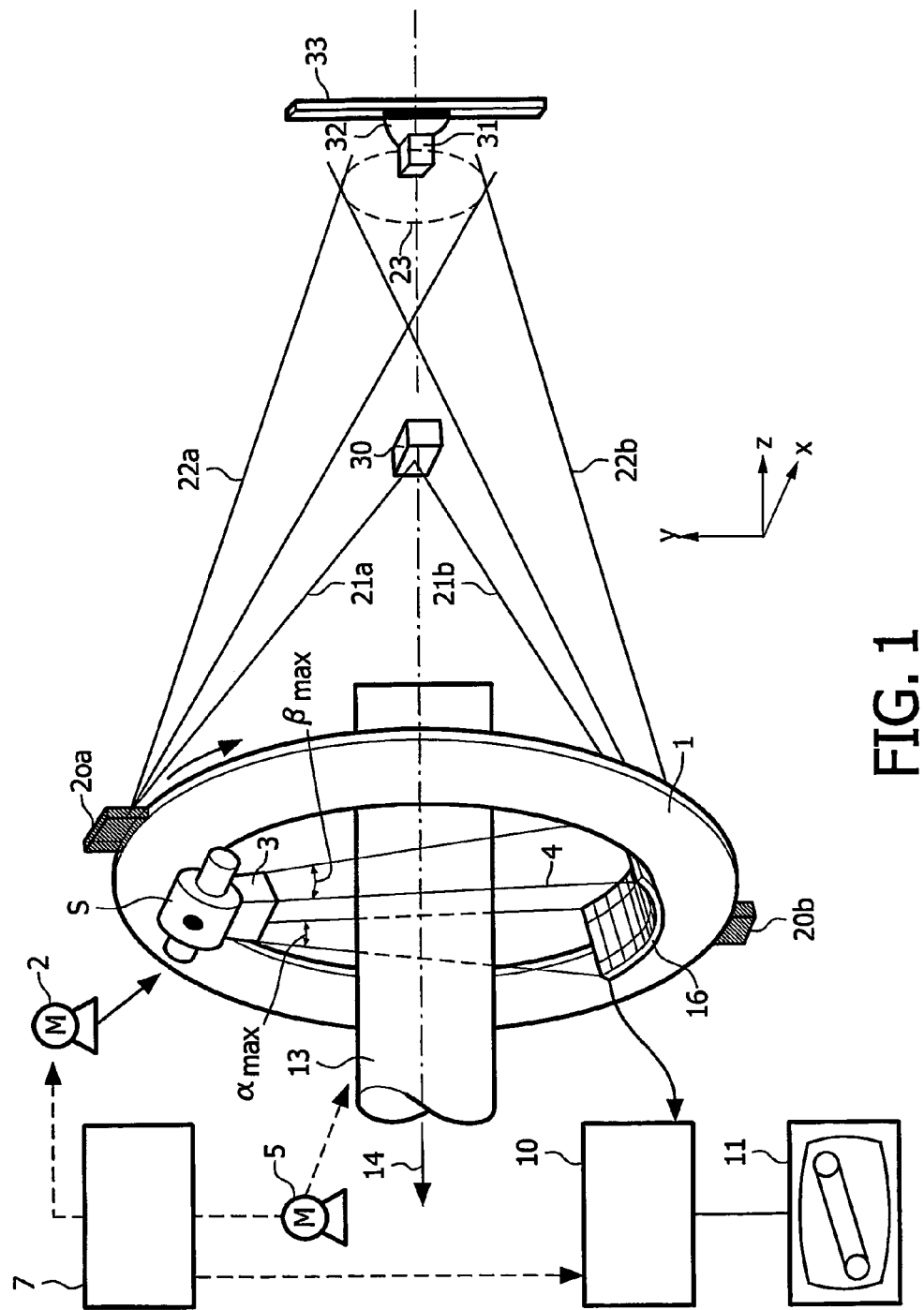
FIG. 1 shows a computer tomograph according to the invention.

The computer tomograph illustrated in FIG. 1 can be used, for example, in medicine for producing sectional images or volume images of patients, or for baggage inspection at airports. It comprises a gantry, the rotor 1 of which is illustrated schematically and can rotate about an axis of rotation 14 running parallel to the z-direction. For the sake of clarity, the stator is not illustrated here. Also not illustrated is a housing, which is in the form of a flat tube and accommodates the rotor and the stator. For rotation, the rotor 1 is driven by a motor 2 at a preferably constant yet adjustable angular speed. A beam source S, for example an X-ray tube, is fixed to the rotor 1. The beam source is provided with a collimator arrangement 3, which extracts a conical beam bundle 4 from the radiation produced by the beam source S. The beam bundle 4 passes through an object, not shown more specifically, which is located in a cylindrical examination region 13. After passing through the examination region 13, the X-ray bundle 4 impinges on a two-dimensional detector unit 16, which is fastened to the rotor 1 and is curved consistent with the contour of the rotor 1. Additionally or alternatively, the detector unit 16 can be constructed so that the X-radiation scattered by the object is detected.

The first angle of aperture of the beam bundle 4 denoted by $\alpha_{max}$ (angle that a ray of the bundle 4 situated at the edge in the x-y plane encloses with a plane defined by the beam source S and the axis of rotation 14) then determines the diameter of the examination region 13, within which the object to be examined must be located during acquisition of the measured values. The angle of aperture of the beam bundle 4 denoted by $\beta_{max}$ (angle that is formed by the two outermost rays in the z-direction in a plane defined by the beam source S and the axis of rotation 14) then determines the thickness of the examination region 13, within which the object to the examined must be located during acquisition of the measured values.

The measurement data acquired by the detector unit 16 is supplied to the transmitters 20a and 20b, which transmit light modulated with the measurement data in the form of respective light beams 21a and 21b. Each of the transmitters 20a and 20b contains here one or more transmitter units such as light-emitting diodes, lamps or laser diodes. If necessary, additional means for optically influencing the light transmitted by the transmitter, such as lenses or reflectors, can be provided in the transmitters 20a and 20b. Depending on the type of transmitter units and the optical means used, the light is transmitted in the form of a light beam 21a and 21b or in the form of a cone of light 22a or 22b. To start with, transmitters that transmit the light in the form of a light beam, as is the case, for example, with transmitters with laser light, will be considered. The modulation of the light corresponding to the data to be transmitted is effected according to known methods, which can be found in the technical literature. For example, at least four effects and modulators are known for modulation: electro-absorption, the electro-optical modulator, Pockels cell and the acousto-optical modulator. These effects and modulators and also corresponding laser transmitters and their properties are described in the document "Basic Note DWDM Systems", Profile Optische-Systeme GmbH, May 2000, rendering any need to go into further details unnecessary here. If, as illustrated in FIG. 1, a plurality of transmitters that transmit the same information is used, then care should be taken that the modulation of the individual transmitters takes place at least almost in the same phase.

So that the light beams are able to reach the receiver 30, the housing (not illustrated) is provided with an annular slot, which is optionally filled with a translucent disc. The transmitters 20a and 20b are each provided with adjusting devices, not illustrated, such as adjusting screws, in order to be able to adjust the direction of the respective light beam 21a or 21b exactly to the position of the receiver 30. In order to prevent the light beam 21a or 21b from being unable to be received by the receiver 30 as a result of adjustment errors, which also include misalignments during operation that are caused, for example, by vibration, it is wise to use a receiver according to FIG. 2.

Such a receiver contains a diffusion disc 40, on which, for example, the light beam 21a impinges. Through known effects, the light of the light beam 21a is distributed in the diffusion disc 40 around the point of incidence of the light beam 21a over a circular area 41, here indicated in FIG. 2 by the dark line. Behind the diffusion disc there is first of all a first receiving element 42, for example, a photodiode, a phototransistor or other known light-sensitive components. If the light beam 21a impinges on the diffusion disc exactly at the point of intersection of the diffusion disc 40 with the axis of rotation 14, then on rotation of the rotor 1 the position of the circular area 41 on the diffusion disc does not change. If, owing to misalignment of the transmitter 20a, the light beam 21a impinges on the diffusion disc 40 somewhat offset from the point of intersection, then the circular area 41 travels on the diffusion disc around the point of intersection corresponding to the rotary movement. Centrally with respect to the point of intersection a likewise circular region then forms, in which the light is still scattered, irrespective of the angle of rotation, and behind which the receiving element 42 is mounted. Up to a certain degree of misalignment it is therefore ensured that the receiver 42 always receives light.

Figure 2:
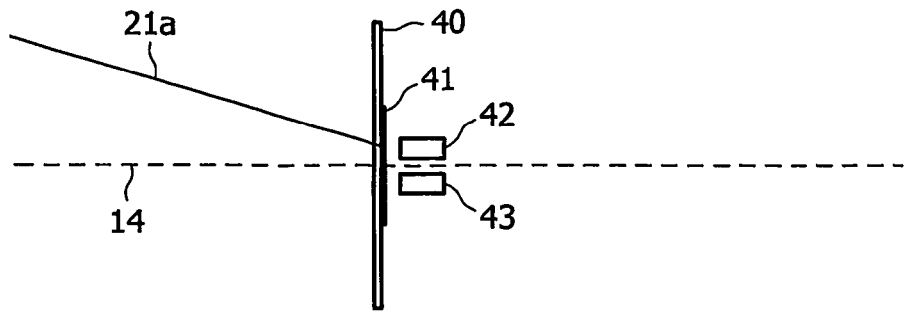
FIG. 2 shows a first construction of a receiving unit.
Figure 3:
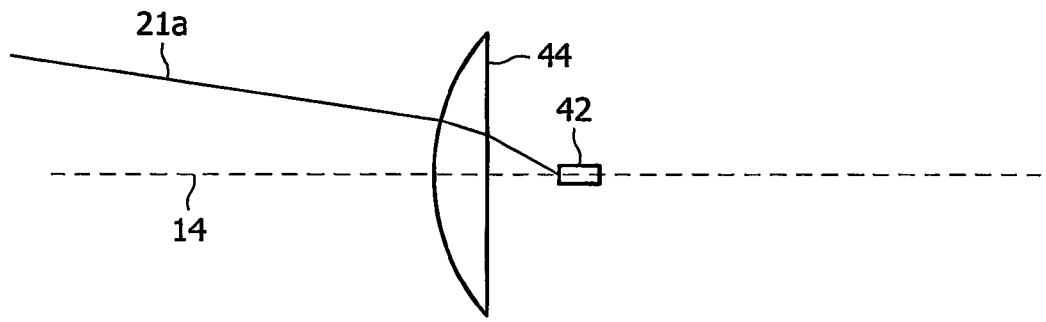
FIG. 3 shows a second construction of a receiving unit.

Instead of the receiver from FIG. 2, a receiver such as that illustrated in FIG. 3 can be used. Here, instead of the diffusion disc 40, a lens 44 is located between the light beam 21a and the receiving element 42. The lens is designed so that an incident light beam is deflected to the receiving part 42 regardless of its point of incidence on the lens. As an alternative to a lens 44, a Fresnel lens can be used. A combination of the receivers from FIG. 2 and FIG. 3 is also conceivable.

The transmitters 20a and 20b from FIG. 1 can alternatively contain a plurality of transmitter units that transmit light with respective different spectral regions, for example, laser diodes having different wavelengths or light sources having different filters. To modulate the light, respective different data can then be used for each transmitting unit, so that a plurality of parallel channels is available for data transfer. The transmitter units are arranged in such close proximity to one another that in the Figures the corresponding individual light beams are taken jointly as light beams 21a or 21b. With the receiver from FIG. 2, the light of such a multi-channel transmitter can be received when a separate receiver unit for each channel, respectively for each spectral region, is arranged behind the diffusion disc 40. Two receiver units 42 and 43 are illustrated in FIG. 2.

To realize a plurality of parallel channels, is it also possible for the transmitters 20a and 20b to contain, for example, two transmitter units, of which the one transmits its light beam 21a respectively 21b in the direction of the receiver 30 and the other transmits its light beam (not illustrated here) in the direction of the receiver 31.

As indicated above, the transmitters 20a and 20b can also be designed so that they transmit light in the form of cones of light 22a and 22b. For that purpose, the transmitters can each contain a light source with a reflector and a lens system. Alternatively, however, a laser light source with known means for widening the light beam to a cone of light can be used. Where it impinges on the receiver 31, the respective cone of light 22a and 22b is intended to have a cross-sectional area 23 that is at least as large as the light-receiving area of the receiver. If the cross-sectional area 23 is nevertheless larger, then problems arising from a possible misalignment of the transmitters 20a and 20b are avoided, compare in this respect the description relating to FIG. 2.

In FIG. 1, the light received by the receiver 30 and/or 31 is first of all demodulated by a unit, not illustrated, in the receiver. The measurement data then available subsequently pass to the reconstruction unit 10, which from the measurement data reconstructs the absorption distribution in the part of the examination region 13 covered by the beam cone 4. On one revolution of the rotor 1, the object to be examined is fully penetrated by the beam bundle 4, with the result that per revolution a respective two-dimensional or three-dimensional image data record can be generated and displayed on the monitor 11.

The motor 2, the reconstruction unit 10, the beam source S and the transfer of the measurement data from the detector unit 16 to the reconstruction unit 10 are controlled by a suitable control unit 7. If the object to be examined is larger in the z-direction that the extent of the beam bundle 4, then the examination region can be displaced by means of a motor 5, which is likewise controlled by the control unit 7, parallel to the direction of the axis of rotation 14 and the z-axis. Control of the motors 2 and 5 can be effected in such a way that the ratio of speed of advancement of the examination region 13 and the angular speed of the rotor 1 are in a constant ratio.

Assuming that a person approaches the computer tomograph so that with the transmitters 20a and 20b positioned horizontally he/she masks the light 21a or 21b transmitted by one of the transmitters, when the rotor rotates, the light of the transmitters 20a and 20b is alternately masked by this person and at the same time the light of the respective other transmitter is not masked. The transmitters 20a and 20b and the corresponding receiver 30 are designed so that the light intensity of just one transmitter 20a or 20b is sufficient to transfer the data. Even with the light of one transmitter 20a or 20b masked, a data transfer is therefore ensured. In the case of a computer tomograph for baggage inspection, it is thus possible to introduce the baggage on a conveyor belt from the left-hand side into the computer tomograph, examine it, and then let it fall on the right-hand side onto a conveyor belt at a lower level, or to transport it out of the computer tomograph by way of a conveyor belt running obliquely downwards between rotor 1 and receiver 30 (the distance between rotor 1 and receiver 30 in FIG. 1 is not to scale). In this case, the light beams 21a and 21b are admittedly alternately regularly interrupted by the item of baggage and possibly also by the obliquely running conveyor belt, but the data transfer is ensured by the respective other transmitter whose light beam is not masked.

Computer tomographs are known in which the gantry is pivotable. Even in the case of such computer tomographs, corresponding transmitters and receivers can be used. It is assumed that in FIG. 1 the gantry, not illustrated, is constructed to pivot about the x-axis (corresponding components are not illustrated), so that during pivoting the rotor 1 and the axis of rotation 14 likewise rotate about the x-axis, whereas the receivers 30 or 31 remain in their position. If the transmitters 20a and 20b each transmit a respective conical light beam 22a and 22b, the gantry can be pivoted until the receiver 31 is located at the edge of the area 23. If the gantry is now pivoted even further, then the receiver 31 is no longer able to receive light. One possibility is to provide the receiver 31 with a drive unit 32, which is controlled by the control unit 7 in such a way that the receiver 31 is moved on a rail 33 in accordance with the pivoting of the gantry, so that the light of the transmitters 20a and 20b is able to reach the receiver. If the gantry can additionally be pivoted about the y-axis, then the positioning device for the receiver 31 can be of correspondingly two-dimensional design. Naturally, the receiver 30 can also be equipped with a positioning device.

Figure 4:
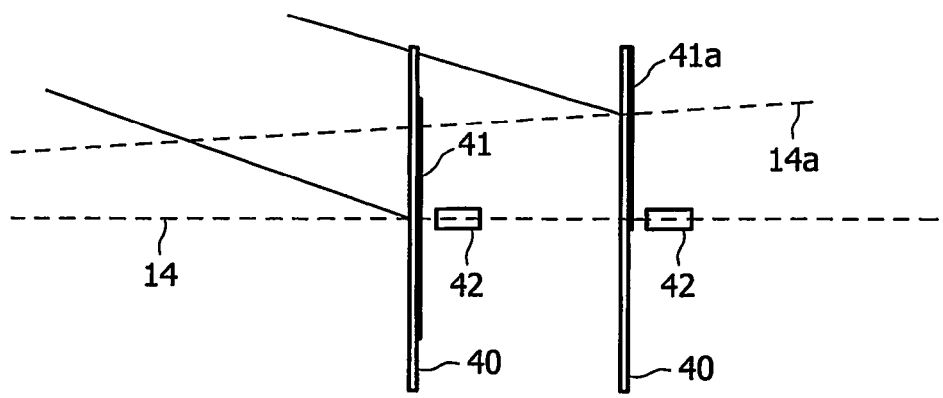
FIG. 4 shows a third construction of a receiving unit with a pivotable gantry.

As an alternative to a positioning device, it is also possible in the case of pivotable gantries to use a receiver according to FIG. 2, especially in the case of line-form light beams such as light beam 21a. In that case, by appropriate construction of the diffusion disc one must ensure that on the one hand the light beam 21a always impinges on the diffusion disc even with the gantry pivoted, and that on the other hand the diffusion disc scatters the light beam 21a over a sufficiently large area. This is illustrated in FIG. 4 in the first place using the left-hand diffusion disc 40. In the non-tilted state of the gantry, the axis of rotation 14 runs approximately centrally through the left-hand diffusion disc 40. The incident light beam is scattered onto the area 41 and received by the receiving element 42. The tilted state of the gantry is illustrated in FIG. 4 using the right-hand diffusion disc 40. The axis of rotation 14 has altered its position relative to the diffusion disc and is now represented as axis of rotation 14a, with the result that the scattered area 41a has been displaced upwards compared with the area 41. The size of the area 41a, however, is configured so that the receiving element 42 can still receive scattered light. If the gantry is pivotable only about one axis, then the diffusion disc 40 can be in the form of a rectangular strip.

The invention claimed is:

1. A computer tomograph,
    having a gantry, which contains a rotor rotating in the operating state about an axis of rotation and from which data is transferred,
    having at least one transmitter attached to the rotor for transmitting light in the direction of the axis of rotation, the light being modulated with the data,
    having at least one receiver mounted on the axis of rotation for receiving the light transmitted through free space by the transmitter.

2. A computer tomograph as claimed in claim 1, having at least two transmitters, which are attached to the rotor offset with respect to one another.

3. A computer tomograph as claimed in claim 1, having a transmitter that transmits the light in at least two different directions.

4. A computer tomograph as claimed in claim 1, in which the spectrum of the transmitted light is divided into a plurality of regions and the light of at least two of the respective regions is modulated with different data.

5. A computer tomograph as claimed in claim 4, in which each transmitter transmits the light of one region.

6. A computer tomograph as claimed in claim 4, in which a transmitter transmits light from a plurality of regions.

7. A computer tomograph as claimed in claim 1, in which the receiver comprises optical means for deflecting and/or scattering the light beams.

8. A computer tomograph as claimed in claim 1, in which the transmitter transmits laser light.

9. A computer tomograph as claimed in claim 4, in which the receiver is able to receive a plurality of spectral regions of the transmitted light separately from one another.

10. A computer tomograph as claimed in claim 1 having a plurality of receivers, which are arranged in succession on the axis of rotation.

11. A computer tomograph as claimed in claim 1 having a pivotable gantry and means for holding the position of the receiver on the axis of rotation when performing the pivoting movement.

* * * * *